US009555237B2

(12) United States Patent
Self

(10) Patent No.: US 9,555,237 B2
(45) Date of Patent: Jan. 31, 2017

(54) OVERVOLTAGE PROTECTION CIRCUITRY

(71) Applicant: Medtronic, Inc., Minneapolis, MN (US)

(72) Inventor: Shane A. Self, Mesa, AZ (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/693,358

(22) Filed: Apr. 22, 2015

(65) Prior Publication Data

US 2015/0306383 A1    Oct. 29, 2015

Related U.S. Application Data

(60) Provisional application No. 61/983,210, filed on Apr. 23, 2014.

(51) Int. Cl.
| | |
|---|---|
| *A61N 1/05* | (2006.01) |
| *A61N 1/36* | (2006.01) |
| *H02H 9/02* | (2006.01) |
| *A61N 1/08* | (2006.01) |
| *H02H 9/04* | (2006.01) |
| *A61N 1/14* | (2006.01) |
| *A61N 1/37* | (2006.01) |

(52) U.S. Cl.
CPC ............. *A61N 1/08* (2013.01); *A61N 1/0534* (2013.01); *A61N 1/14* (2013.01); *A61N 1/36* (2013.01); *A61N 1/3605* (2013.01); *A61N 1/36125* (2013.01); *A61N 1/36142* (2013.01); *H02H 9/045* (2013.01); *A61N 1/3718* (2013.01)

(58) Field of Classification Search
CPC .......... A61N 1/08; A61N 1/0534; A61N 1/14; A61N 1/3612; A61N 1/36142; H02H 9/02; H02H 9/045; H02H 9/04; H02H 3/20
See application file for complete search history.

(56) References Cited

U.S. PATENT DOCUMENTS

| 3,558,979 | A | * | 1/1971 | Lorenz | ................... H02H 9/041 330/112 |
|---|---|---|---|---|---|
| 3,571,660 | A | * | 3/1971 | Phillips | .................. H02H 9/041 361/111 |
| 3,968,802 | A | | 7/1976 | Ballis | |
| 4,038,990 | A | | 8/1977 | Thompson | |
| 4,213,098 | A | * | 7/1980 | Tsividis | .............. H03F 3/45183 330/253 |

(Continued)

FOREIGN PATENT DOCUMENTS

JP    2009106128 A    5/2009

OTHER PUBLICATIONS

"MOSFET Capacitances," 97.477 Lecture, retrieved from http://www.docs-library.com/pdf/1/1/ieee-1490-2003.html, lecture dated Jan. 13, 2003, 13 pp.

(Continued)

*Primary Examiner* — William Levicky
(74) *Attorney, Agent, or Firm* — Shumaker & Sieffert, P.A.

(57) ABSTRACT

Overvoltage protection circuitry configured to protect internal integrated circuits within an implantable device in the presence of a high voltage event such as defibrillation or electrocautery. The circuitry allows for an internal node to rise above the voltage level of the high voltage event to insure that an overvoltage protection element is triggered, even if the voltage level of the high voltage event is below the voltage trigger level of the overvoltage protection element.

21 Claims, 7 Drawing Sheets

(56) References Cited

U.S. PATENT DOCUMENTS

| | | | |
|---|---|---|---|
| 5,649,965 A | | 7/1997 | Pons et al. |
| 5,696,391 A | * | 12/1997 | Bernier ............... H01L 27/0248 257/120 |
| 5,761,019 A | * | 6/1998 | Kroll ...................... H02H 9/025 128/908 |
| 6,546,287 B1 | | 4/2003 | Havel et al. |
| 7,098,717 B2 | | 8/2006 | Watt |
| 2008/0183230 A1 | | 7/2008 | Kemmetmueller et al. |
| 2010/0087897 A1 | * | 4/2010 | Gromotka ................ A61N 1/08 607/63 |
| 2010/0114211 A1 | | 5/2010 | Donofrio et al. |
| 2011/0093041 A1 | | 4/2011 | Straka et al. |
| 2011/0133247 A1 | | 6/2011 | Sarbishaei et al. |
| 2011/0288615 A1 | | 11/2011 | Armstrong et al. |
| 2013/0208383 A1 | | 8/2013 | Maile et al. |
| 2014/0036399 A1 | * | 2/2014 | Ory ......................... H01L 23/62 361/56 |
| 2015/0222349 A1 | * | 8/2015 | Sloan ................. H04B 7/15528 455/7 |

OTHER PUBLICATIONS

"3.2 Transistor Parasitic Capacitance," Application-Specific Integrated Circuits, retrieved on Oct. 17, 2013, from http://iroi.seu.edu.cn/books/asics/Book2/CH03/CH03.2.html, 8 pp.

"MOS Capacitor," Hu_Ch05v3.fm, retrieved from http://www.eecs.berkeley.edu/~hu/Chenming-Hu_ch5.pdf, chapter dated Feb. 13, 2009, 38 pp.

Madigan, et al., "Surgical Management of the Patient with an Implanted Cardiac Device," Annals of Surgery, vol. 230, No. 5, May 10, 1999, pp. 639-647.

International Search Report and Written Opinion from International Application No. PCT/US2015/027132, dated Jul. 2, 2015, 13 pp.

International Preliminary Report on Patentability from International Application No. PCT/US2015/027132, dated Nov. 3, 2016, 9 pp.

\* cited by examiner

OVERVOLTAGE PROTECTION CIRCUITRY

This application claims the benefit of U.S. Provisional Application Ser. No. 61/983,210, entitled "OVERVOLTAGE PROTECTION CIRCUITRY," filed on Apr. 23, 2014, the entire content of which is incorporated herein by reference.

TECHNICAL FIELD

The disclosure relates to protecting integrated circuitry in medical devices from damage due to electrical currents.

BACKGROUND

A variety of medical devices for delivering a therapy and/or monitoring a physiological condition have been used clinically or proposed for clinical use in patients. Examples include medical device that delivery therapy and/or monitor conditions associated with the heart, muscle, nerve, brain, stomach, or other organs or issues. Some therapies include the delivery of electrical signals, e.g., stimulation, to such organs or tissues. Some medical devices may employ one or more elongated electrical leads carrying electrodes for delivery of therapeutic electrical stimulation to such organs or tissues. In some examples, a lead may include electrodes that sense intrinsic electrical signals within the patient and/or other sensors for sensing physiological parameters of a patient. Other medical devices do not include leads, and instead include electrodes and/or sensors formed on or located within a housing of the device. In some examples, the medical device may be an implantable medical device (IMD).

Patients requiring delivery of electrical stimulation may also require other therapeutic or diagnostic devices or procedures. In some examples, such as the use of magnetic resonance imaging (MRI), the application of a defibrillation pulse, or the use of cauterizing equipment during surgical procedures, there is a risk of damage to circuitry within an IMD due to the additional therapeutic or diagnostic devices or procedures. In particular, the additional therapeutic or diagnostic procedure may generate large amount of electrical current that can cause damage to circuitry within the IMD.

SUMMARY

The disclosure is generally directed to circuitry including overvoltage protection circuitry configured to protect internal integrated circuitry in a medical device from the large voltages or currents generated by other devices or procedures.

In some examples consistent with this disclosure, a medical device comprises a first implantable electrode; a second implantable electrode; a current source configured to source electrical stimulation via the first implantable electrode; a current sink configured to sink the electrical stimulation via the second implantable electrode; a capacitor configured to receive, via at least one of the current source and current sink, current generated by a first voltage across the first implantable electrode and the second implantable electrode, and store a second voltage with the received current; and an overvoltage protection element configured to shunt current from at least one of the first implantable electrode and second implantable electrode if the second voltage stored by the capacitor exceeds a threshold voltage of the overvoltage protection element.

In some examples consistent with this disclose, a method comprises detecting a first voltage between a first implantable electrode and a second implantable electrode, the first voltage generating a current; creating a current path between the first implantable electrode, a current source configured to source electrical stimulation via the first implantable electrode; a current sink configured to sink the electrical stimulation via the second implantable electrode; and the second implantable electrode, wherein a respective capacitive characteristic associated with each of the current source and the current sink creates a respective portion of the current path to the capacitor; storing at the capacitor, a second voltage from the current received at the capacitor via the current path; and activating an overvoltage protection element configured to shunt current from at least one of the first implantable electrode and second implantable electrode if the second voltage stored by the capacitor exceeds a threshold of the overvoltage protection element.

In some examples consistent with this disclosure, a circuit comprises a first implantable electrode; a second implantable electrode; a first diode configured to allow current, generated by a first voltage across the first implantable electrode and the second implantable electrode; to flow from the first implantable electrode to an internal node in of the circuit, wherein the internal node is configured to allow a second voltage of the internal node to raise in response to the current generated by the first voltage; a capacitor attached to the internal node and configured to receive, via the internal node, a second current at the internal node and store a third voltage with the received second current; and an overvoltage protection element configured to shunt current from at least one of the first implantable electrode and second implantable electrode if the third voltage store by the capacitor exceed a threshold voltage of the overvoltage protection element.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
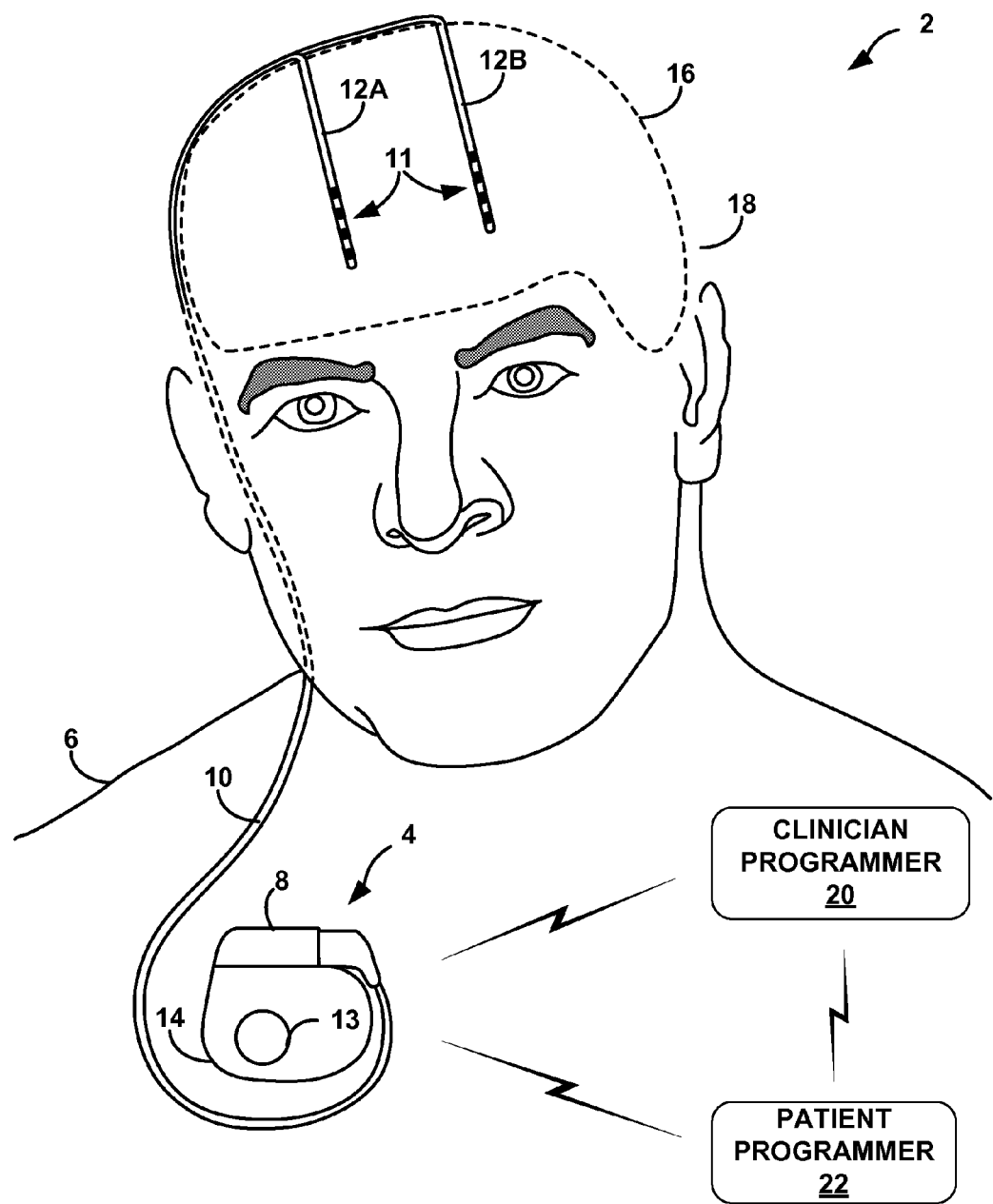
FIG. 1 is a conceptual diagram illustrating an example system that may be used to deliver electrical stimulation therapy to patient.

This disclosure is directed to a medical device that includes overvoltage protection circuitry to protect the integrated circuits within the medical device. Although discussed primarily with respect to an implantable medical device (IMD), the principle of operation is the same for any device which may be exposed to relatively large external voltage or current events. The medical device may be a stimulating device, a sensing device, or both. An IMD includes two or more implantable electrodes through which large levels of current or voltage may be transmitted to the internal integrated circuitry when the IMD is subjected to a large current or voltage from an external device or procedure. The current or voltage may be generated, for example, from delivery of electrocautery energy to tissue of a patient or delivery of a defibrillating shock to the patient's heart. In examples consistent with this disclosure, the IMD may include an overvoltage protection element. In some examples, the current or voltage may be sufficient to trigger the overvoltage protection element to clamp the voltage to the internal integrated circuitry, thereby protecting the internal circuitry. In other examples, the high voltage or current event may not give rise to a voltage sufficient to trigger the overvoltage protection. However, the voltage or current may be sufficient to damage internal integrated circuitry is left unclamped. In examples consistent with the disclosure, the IMD may include an internal node which allows for a capacitor to charge to a level greater than the voltage at the electrodes in the presence of a high voltage in order to raise the voltage at the overvoltage protection element to a level sufficient to trigger the overvoltage protection element. Once triggered, the overvoltage protection circuitry clamps the voltage to the internal integrated circuit. If the circuitry within IMD is not configured properly to trigger the overvoltage protection circuitry even when the stimulus in not as high at the trigger voltage, then the stimulation integrated circuit may act as a pseudo clamp allowing excessive current to cause damage to the integrated circuit.

In some examples the overvoltage protection circuitry may comprise a triggering circuit and a protection element. In other examples, the overvoltage protection circuitry may include an overvoltage protection element which automatically triggers when a voltage at the overvoltage protection element is above a predetermined level. For example, the overvoltage protection element may be a silicon-controlled rectifier (SCR) type device which is activated (or "breaks over") at a predetermined voltage, allowing current to be shunted. Once the SCR is activated, it will remain in the activated state as long as a current at the SCR is above a predetermined level, even if the voltage is not longer at the level needed to activate the SCR. The current needed to maintain the SCR in an active state may be called a hold current. The hold current may between approximately 1 mA and 10 mA. The hold current may be the current from an outside source such as defibrillation or electrocautery that is not shunted by the overvoltage protection element. In some examples the current corresponding to the voltage from the external source may be above approximately 40 mA prior to the SCR being activated.

In some examples consistent with this disclosure, the IMD may include a current source, such as a current cascode, configured to source electrical stimulation via a first one of the electrodes and a current sink, such as a sink cascode, configured to sink electrical stimulation via a second one of the implantable electrodes. The presence of both a current source and a current sink allows for the IMD to provide bipolar stimulation in a unipolar mode. In some examples, the current source includes at least one PMOS transistor and the current sink includes at least one NMOS transistor. Although discussed with respect to an example with a first and second electrode, in some examples, a plurality of electrodes each with their own associated sources and sinks may be present in the IMD. In such instances, the individual sources and sink may include respective circuitry for overvoltage protection. Further, in some examples, a given electrode may be selectively coupled to a source or a sink.

In some examples, the PMOS and NMOS transistors are configured within a circuit such that when a large voltage, which is below a threshold voltage of the overvoltage protection element, is applied to implantable electrodes of the circuit, a current path is created between the implantable electrodes, the transistors, and a capacitor. In some examples, the capacitor is configured to collect current over time in order to increase the voltage at the overvoltage protection element in order to reach the threshold voltage of the overvoltage protection element thereby triggering the overvoltage protection. The current source and sink PMOS and NMOS transistors aid in the charge of an internal node connected to the capacitor. In some examples, the charging of the capacitor above a predetermined threshold voltage level of an overvoltage protection element serves to activate the overvoltage protection element, which then clamps the voltage across the electrodes to be less than a protection voltage level. In some examples, the overvoltage protection element may clamp the voltage across the electrodes to be less than approximately 4 volts, or less than approximately 3 volts, thereby protecting the integrated circuitry within the IMD from the large voltage event.

In some examples, a current path is created by activating a PN junction within the PMOS transistor which is not activated during the application of a stimulation pulse via the respective electrode. Similarly, another PN junction within the NMOS transistor may also be activated which is not activated during the application of a stimulation pulse via the respective electrode. The current path within the current source transistor may be activated when the voltage at the node connected to the electrode exceeds the voltage at the node connected to the capacitor by approximately a diode bias potential. The current path within the current sink transistor may be activated when voltage difference between the electrode node and the capacitor node exceeds approximately a diode bias potential.

In some examples, a current path between the implantable electrodes, the overvoltage protection element and the capacitor may include actual diodes. In such configurations the diodes may be included in the circuit next to the current source transistor and current sink transistors. The diodes may be configured to allow current to flow in the opposite direction as the current source transistor and the current sink transistor, thereby creating a current path to an internal node including the capacitor when a high enough voltage is present at the implantable electrodes.

FIG. 1 is a conceptual diagram illustrating an example system 2 that may be used to deliver stimulation therapy to patient 6. Patient 6 ordinarily, but not necessarily, will be a human. Generally, therapy system 2 includes implantable stimulator 4 that delivers electrical stimulation to patient 6 via one or more implantable electrodes of electrode array 11.

The implantable electrodes may be deployed on one or more implantable medical leads, such as implantable medical lead 10, and in some cases on a can electrode. The electrical stimulation may be in the form of constant current or voltage pulses or substantially continuous waveforms. Various parameters of the pulses or waveforms may be defined by a stimulation program. The pulses or waveforms may be delivered substantially continuously or in bursts, segments, or patterns, and may be delivered alone or in combination with pulses or waveforms defined by one or more other stimulation programs. Although FIG. 1 shows a fully implantable stimulator 4, techniques described in this disclosure may be applied to external stimulators having electrodes deployed via percutaneously implantable leads. One or more of the electrodes may be located on a housing 14, i.e., "can" or "case," of the implantable stimulator 4. In addition, in some cases, implantable electrodes may be deployed on a leadless stimulator.

In the example illustrated in FIG. 1, implantable stimulator 4 is implanted within a subcutaneous pocket in a clavicle region of patient 6. During implantation, a physician may use one or more tools, such as a cautery in to aid in implantation. Implantable stimulator 4 includes a protection element (not shown) which protects the internal circuitry of implantable stimulator 4 from the high voltage and/or current used in electrocautery, which can enter the circuitry through the electrodes on lead 10, or on housing 14.

Stimulator 4 generates programmable electrical stimulation, e.g., a current waveform or current pulses, and delivers the stimulation via an implantable medical lead 10 carrying an array of implantable stimulation electrodes 11. In some cases, multiple implantable leads may be provided. In the example of FIG. 1, a distal end of lead 10 is bifurcated and includes two lead segments 12A and 12B (collectively "lead segments 12"). Lead segments 12A and 12B each include a set of electrodes forming part of the array of electrodes 11. In various examples, lead segments 12A and 12B may each carry four, eight, or sixteen electrodes. In FIG. 1, each lead segment 12A, 12B carries four electrodes, configured as ring electrodes at different axial positions near the distal ends of the lead segments. Throughout the remainder of this disclosure, for purposes of simplicity, the disclosure may generally refer to electrodes carried on "leads" rather than "lead segments."

FIG. 1 further depicts a housing, or can, electrode 13 carried by housing 14. Housing electrode 13 may be formed integrally with an outer surface of hermetically-sealed housing 14 of implantable stimulator 4, also referred to in this disclosure as implantable medical device (IMD) 4, or otherwise coupled to housing 14. In one example, housing electrode 13 may be described as an active, non-detachable electrode on the surface of the IMD. In some examples, housing electrode 13 is defined by an uninsulated portion of an outward facing portion of housing 14 of IMD 4. Other divisions between insulated and uninsulated portions of housing 14 may be employed to define two or more housing electrodes, which may be referred to as case or can electrodes. In some examples, housing electrode 13 comprises substantially all of housing 14, or a portion of the housing 14. Using the techniques of this disclosure, one or more electrodes 11 may transfer stimulation pulses from the lead 10 to the tissue substantially simultaneously with stimulation pulses delivered via housing electrode 13. Although depicting a configuration wherein IMD 4 is delivering deep brain stimulation, IMD 4 may be used to apply any type of stimulation including, for example, pelvic, gastric, peripheral nerve, or spinal cord stimulation.

In some examples, lead 10 may also carry one or more sense electrodes to permit implantable stimulator 4 to sense electrical signals from patient 6. Some of the stimulation electrodes may be coupled to function as stimulation electrodes and sense electrodes on a selective basis. In other examples, implantable stimulator 4 may be coupled to one or more leads which may or may not be bifurcated. In such examples, the leads may be coupled to IMD 4 via a common lead extension or via separate lead extensions.

A proximal end of lead 10 may be both electrically and mechanically coupled to header 8 on implantable stimulator 4 either directly or indirectly via a lead extension. Conductors in the lead body may electrically connect stimulation electrodes located on lead segments 12 to IMD 4. Lead 10 traverses from the implant site of implantable stimulator 4 along the neck of patient 6 to cranium 18 of patient 6 to access brain 16. Lead segments 12A and 12B are implanted within the right and left hemispheres, respectively, in order to deliver electrical stimulation to one more regions of brain 16, which may be selected based on the patient condition or disorder.

IMD 4 may deliver, for example, deep brain stimulation (DBS) or cortical stimulation (CS) therapy to patient 6 via the electrodes carried by, i.e., located on, lead segments 12 to treat any of a variety of neurological disorders or diseases. Example neurological disorders may include depression, dementia, obsessive-compulsive disorder, and movement disorders such as Parkinson's disease, spasticity, epilepsy, and dystonia. DBS also may be useful for treating other patient conditions, such as migraines and obesity. However, the disclosure is not limited to the configuration of lead 10 shown in FIG. 1, or to the delivery of DBS or CS therapy.

Lead segments 12A, 12B may be implanted within a desired location of brain 16 through respective holes in cranium 18. Lead segments 12A, 12B may be placed at any location within brain 16 such that the electrodes located on lead segments 12A, 12B are capable of providing electrical stimulation to targeted tissue during treatment. Example locations for lead segments 12A, 12B within brain 26 may include the pedunculopontine nucleus (PPN), thalamus, basal ganglia structures (e.g., the globus pallidus, substantia nigra, and subthalmic nucleus), zona inserta, fiber tracts, lenticular fasciculus (and branches thereof), ansa lenticularis, and/or the Field of Forel (thalamic fasciculus). In the case of migraines, lead segments 12 may be implanted to provide stimulation to the visual cortex of brain 16 in order to reduce or eliminate migraine headaches afflicting patient 6. However, the target therapy delivery site may depend upon the patient condition or disorder being treated.

The electrodes of lead segments 12A, 12B are shown as ring electrodes. Ring electrodes are commonly used in DBS applications because they are simple to program and are capable of delivering an electrical field to any tissue adjacent to lead segments 12A, 12B. In other implementations, the electrodes of lead segments 12A, 12B may have different configurations. For example, the electrodes of lead segments 12A, 12B may have a complex electrode array geometry that is capable of producing shaped electrical fields. The complex electrode array geometry may include multiple electrodes (e.g., partial ring or segmented electrodes) around the perimeter of each lead segments 12A, 12B, rather than one ring electrode. In this manner, electrical stimulation may be directed in a specific direction from lead segments 12 to enhance therapy efficacy and reduce possible adverse side effects from stimulating a large volume of tissue. In alternative examples, lead segments 12 may have shapes other than elongated cylinders as shown in FIG. 1. For example, lead segments 12 may be paddle leads, spherical leads, bendable leads, or any other type of shape effective in treating patient 6.

Therapy system 2 also may include a clinician programmer 20 and/or a patient programmer 22. Clinician programmer 20 may be a handheld computing device that permits a clinician to program stimulation therapy for patient 6 via a user interface, e.g., using input keys and a display. For example, using clinician programmer 20, the clinician may specify stimulation parameters, i.e., create programs, for use in delivery of stimulation therapy. Clinician programmer 20 may support telemetry (e.g., radio frequency (RF) telemetry) with implantable stimulator 4 to download programs and, optionally, upload operational or physiological data stored by implantable stimulator 4. In this manner, the clinician may periodically interrogate implantable stimulator 4 to evaluate efficacy and, if necessary, modify the programs or create new programs. In some examples, clinician programmer 20 transmits programs to patient programmer 22 in addition to or instead of implantable stimulator 4.

Like clinician programmer 20, patient programmer 22 may be a handheld computing device. Patient programmer 22 may also include a display and input keys to allow patient 6 to interact with patient programmer 22 and implantable stimulator 4. In this manner, patient programmer 22 provides patient 6 with a user interface for control of the stimulation therapy delivered by implantable stimulator 4. For example, patient 6 may use patient programmer 22 to start, stop or adjust electrical stimulation therapy. In particular, patient programmer 22 may permit patient 6 to adjust stimulation parameters of a program such as duration, current or voltage amplitude, pulse width and pulse rate. Patient 6 may also select a program, e.g., from among a plurality of stored programs, as the present program to control delivery of stimulation by implantable stimulator 4.

In some examples, implantable stimulator 4 delivers stimulation according to a group of programs at a given time. Each program of such a program group may include respective values for each of a plurality of therapy parameters, such as respective values for each of current or voltage amplitude, pulse width, pulse shape, pulse rate and electrode configuration (e.g., electrode combination and polarity). Implantable stimulator 4 may interleave pulses or other signals according to the different programs of a program group, e.g., cycle through the programs, to simultaneously treat different symptoms or different body regions, or provide a combined therapeutic effect. In such examples, clinician programmer 20 may be used to create programs, and assemble the programs into program groups. Patient programmer 22 may be used to adjust stimulation parameters of one or more programs of a program group, and select a program group, e.g., from among a plurality of stored program groups, as the current program group to control delivery of stimulation by implantable stimulator 4.

Implantable stimulator 4, clinician programmer 20, and patient programmer 22 may communicate via cables or a wireless communication, as shown in FIG. 1. Clinician programmer 20 and patient programmer 22 may, for example, communicate via wireless communication with implantable stimulator 4 using RF telemetry techniques known in the art. Clinician programmer 20 and patient programmer 22 also may communicate with each other using any of a variety of local wireless communication techniques, such as RF communication according to the 802.11 or Bluetooth specification sets, infrared communication, e.g., according to the IrDA standard, or other standard or proprietary telemetry protocols. Each of clinician programmer 20 and patient programmer 22 may include a transceiver to permit bi-directional communication with implantable stimulator 4.

Generally, system 2 delivers stimulation therapy to patient 6 in the form of constant current or voltage waveforms or constant current or voltage pulses. The shapes of the pulses may vary according to different design objectives. In the case of current-based stimulation, implantable stimulator 4 regulates current that is sourced or sunk by one or more electrodes, referred to as regulated electrodes. In some examples, one of the electrodes may be unregulated. In such configurations, either the housing electrode 13 or a lead electrode 11 may be the unregulated electrode.

A source current, i.e., an anodal current, may refer to a positive current, i.e., a current having a positive polarity, that flows out of an electrode, e.g., from a regulated current source via a regulated current path to surrounding tissue, or from a reference voltage via an unregulated current path. A sink current, i.e., a cathodal current, may refer to a negative current, i.e., a current having a negative polarity, that flows into an electrode, e.g., from surrounding tissue and is sunk by a regulated current sink via a regulated current path or by a reference voltage via an unregulated current path. Regulated source currents may sum to produce a greater overall source current. Regulated sink currents may sum to produce a greater overall sink current. Regulated source and regulated sink currents may partially or entirely cancel one another, producing a net difference in the form of a net source current or sink current in the case of partial cancellation. An unregulated current path can source or sink current approximately equal to this net difference.

Figure 2:
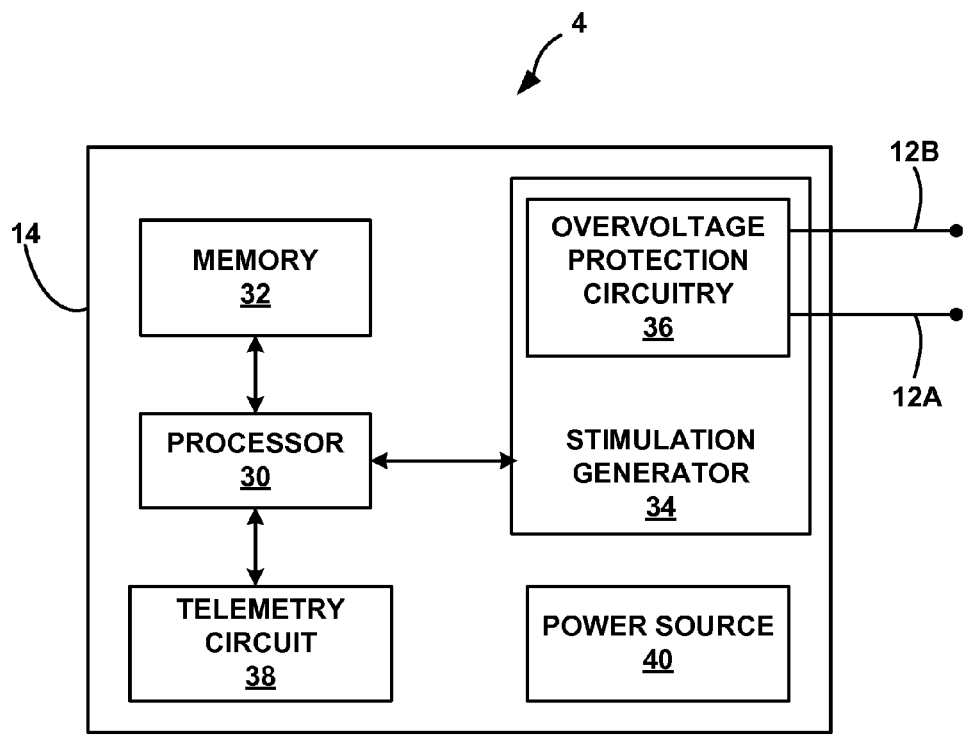
FIG. 2 is a functional block diagram illustrating various example components of an implantable system including an implantable stimulator.

FIG. 2 is a functional block diagram illustrating various example components of an implantable system including an implantable stimulator. Although implantable stimulator 4, lead 10, and lead segments 12 are depicted as a system for providing DBS stimulation, implantable stimulator 4, including overvoltage protection circuitry 36, may be any implantable stimulator, configured to applied stimulation to patient 6.

Implantable stimulator 4 includes a processor 30, memory 32, stimulation generator 34, telemetry circuit 38, and power source 40. Simulation generator 34 includes protection element 36. Memory 32 may store instructions for execution by processor 30, stimulation therapy program data, sensor data, operational and status data, and any other electronic information regarding therapy or patient 6. Such information in memory 32 may assist in determining whether implantable stimulator 4 is currently in a state wherein protection element 36 may be effective. Stimulation program data may include stimulation parameters transmitted from clinician programmer 20 or patient programmer 22, as well as programs defined by such parameters, and program groups. Some data may be recorded for long-term storage and retrieval by a user. Memory 32 may include separate memories for storing different types of data.

In some examples, memory 32 also may store information pertinent to compatibility of implantable stimulator 4 with various situations which may include application of electrocautery or heart defibrillation pulses. For example, memory 32 may store a date on which implantable stimulator 4 and/or leads 12 were implanted in patient 6, a date on which any revision was made to implantable stimulator 4 and/or leads 12, a presence of another IMD implanted in patient 6, or a name and/or phone number of a physician who implanted implantable stimulator 4 or manages care of patient 6. In some examples, memory 32 may store a manufacturer of implantable stimulator 4 and contact information for the manufacturer, an identifier of implantable stimulator 4 and/or leads 12, such as a serial number, model number, registration number, name, or the like, and/or an electrical pulse magnitude to which implantable stimulator 4 can be exposed. Additionally or alternatively, memory 32 may store information regarding an implant location of implantable stimulator 4 and/or leads 12, an indication of the presence of an abandoned, broken, or damaged lead 12, or an impedance of one or more of leads 12 (and, if present, lead extensions or adaptors).

Processor 30 controls stimulation generator 34 to deliver electrical stimulation via electrode combinations formed by electrodes in one or more electrode arrays. For example, stimulation generator 30 may deliver electrical stimulation therapy via electrodes of one or more leads 12, e.g., as stimulation pulses or continuous waveforms. Stimulation generator 34 may include stimulation generation circuitry to generate stimulation pulses or waveforms and switching circuitry to switch the stimulation across different electrode combinations, e.g., in response to control by processor 30. In particular, processor 30 may control the switching circuitry on a selective basis to cause stimulation generator 34 to deliver electrical stimulation to selected electrode combinations and to shift the electrical stimulation to different electrode combinations. Alternatively, in some examples, stimulation generator 34 may include multiple current or voltage sources to control delivery of stimulation energy to selected combinations of electrodes carried by leads 12.

Electrode combinations and other parameters associated with different therapy programs may be represented by data stored in a memory location, e.g., in memory 32, of implantable generator 4. Processor 30 may access the memory location to determine the electrode combination for a particular program and control stimulation generator 34 to deliver electrical stimulation via the indicated electrode combination. Each program may specify a set of parameters for delivery of electrical stimulation therapy. As an example, a program may specify electrode combination, electrode polarities, current or voltage amplitude, pulse rate and pulse width. Additional parameters such as duty cycle, duration, and delivery schedule also may be specified by a therapy program. Processor 30 may control one or more switches (not shown) in order to adjust the internal circuitry so that protection element 36 may be activated when stimulation is not being applied.

Using an external programmer, such as programmer 20, a user may select individual programs for delivery on an individual basis, or combinations of programs for delivery on a simultaneous or interleaved basis. In addition, a user may adjust parameters associated with the programs. The programs may be stored in memory 32 of IMD 4. Alternatively, the programs may be stored in memory associated with external programmer 20. In either case, the programs may be selectable and adjustable to permit modification of therapy parameters. In some examples, patient programmer 22 may allow patient 12 to select among programs programmed by a clinician and stored in a memory of IMD 4 or the patient programmer. Additionally or alternatively, a patient programmer 22 may allow patient 12 to adjust therapy parameters within a range determined by a clinician and stored in memory of the patient programmer or IMD 4. In addition, physician programmer 20 may permit generation of new programs, which may be loaded into memory 32, and adjustment of parameters associated with existing programs.

Upon selection of a particular program or program group from memory 32, processor 30 may control stimulation generator 34 to deliver stimulation according to the programs in the groups, e.g., simultaneously or on a time-interleaved basis. A group may include a single program or multiple programs, each of which specifies an electrode combination. Again, the electrode combination may specify particular electrodes in a single array or multiple arrays, e.g., on a single lead or among multiple leads.

IMD 4 may be responsive to adjustments of programming parameters and electrode configurations by a user via programmer 20. In particular, processor 30 may receive adjustments to program parameters from programmer 20 via telemetry circuit 38. Telemetry circuit 38 may support wireless telemetry with external programmer 20 or another device by radio frequency (RF) communication, proximal inductive interaction of IMD 4 with external programmer 20, or other techniques. Telemetry circuit 38 may send information to and receive information from external programmer 20 on a continuous basis, at periodic intervals, or upon request from the stimulator or programmer. To support RF communication, telemetry circuit 38 may include appropriate electronic components, such as amplifiers, filters, mixers, encoders, decoders, modulators, demodulators and the like. In some examples, processor 30 also may communicate information to programmer 20 or another external device via telemetry circuit 38.

In some examples, IMD 4 may have two operating modes. IMD 4 may automatically switch between the two modes. For example, IMD 4 may be in a "normal" stimulation mode or a non-stimulation mode. During the non-stimulation mode processor 30 may suspend therapy delivery and enter a state wherein overvoltage protection circuitry 36 may be activated. Processor 30 may switch from a normal, or stimulation, operating mode, in which stimulation generator 34 delivers therapy to patient 6 via electrodes carried by leads 12, to a non-stimulation mode in response to an instruction received from an external device, such as, for example, programmer 20. In some examples, processor 30 may control the components of IMD 4 to automatically switch back to the non-stimulation mode, in which overvoltage protection circuitry 36 may be activated, between each stimulation pulse from stimulation generator 34. The automatic switching between a stimulation mode and a non-stimulation mode may prevent damage by an unexpected electrical pulse delivered to patient 6. In the non-stimulation mode mode, according to some examples, IMD 4 remains awake (operational) but does not actively deliver electrical stimulation to the patient, and the overvoltage protection circuitry 36 is in a state to be activated upon detection of an electrical pulse.

Overvoltage protection circuitry 36 may be a silicon-controlled rectifier for example. When IMD 4 is in a non-stimulation mode the overvoltage protection circuitry has a voltage threshold trigger whereby the overvoltage protection element 36 clamps the voltage at a predetermined level once the threshold is reached and maintains the clamp as long as the current level across the protection element 36 is maintained. In some examples, the voltage threshold may be between approximately 17 volts and approximately 24 volts. In some examples, the voltage threshold may be approximately 19 volts. In some examples, the current associated with the overvoltage protection element 36 voltage threshold is approximately 40 mA. When the overvoltage protection element 36 is in the on-state, the voltage between the two implantable electrodes is approximately 3 V. In some examples, the current between the two implantable electrodes when the overvoltage protection element 36 is in the on-state the current is approximately 1 mA. In some examples, there is a delay between the voltage at the overvoltage protection element 36 and the overvoltage protection element 36 turning on. In some examples, the delay may be approximately 6 microseconds.

Power source 40 delivers operating power to the components of implantable stimulator 4. Power source 40 may include a small rechargeable or non-rechargeable battery and a power generation circuit to produce the operating power. Recharging may be accomplished through proximal inductive interaction between an external charger and an inductive charging coil within IMD 4. In some examples, power requirements may be small enough to allow IMD 4 to utilize patient motion and implement a kinetic energy-scavenging device to trickle charge a rechargeable battery. In other examples, traditional non-rechargeable batteries may be used for a limited period of time. As a further alternative, an external inductive power supply could transcutaneously power IMD 4 when needed or desired.

Figure 3:
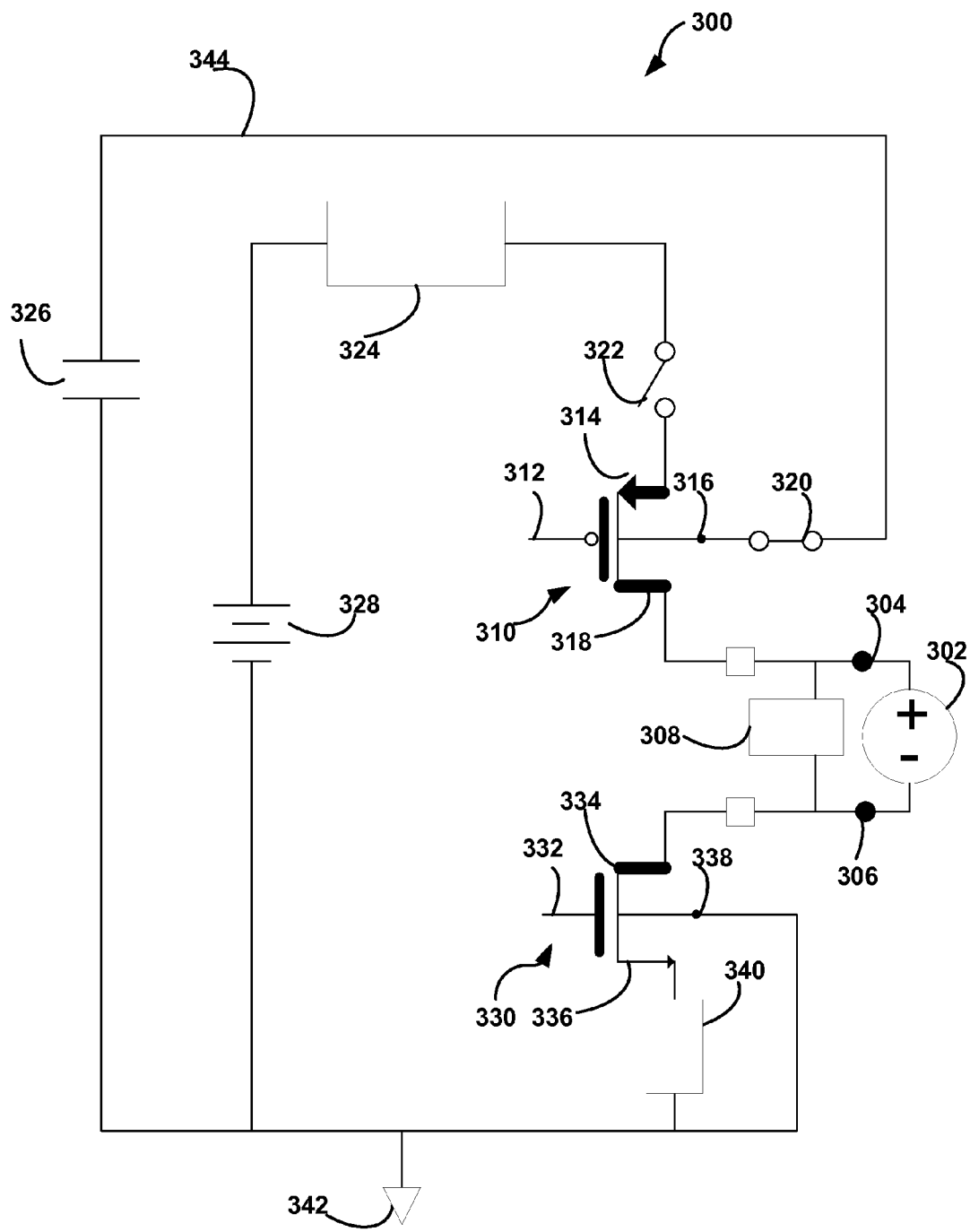
FIG. 3 is a schematic diagram of an example circuit within an implantable stimulator including overvoltage protection circuitry, consistent with this disclosure.

FIG. 3 is a schematic diagram of an example circuit 300 within implantable stimulator 4, including overvoltage protection circuitry, consistent with this disclosure. Example circuit 300 is simplified to primarily show the configuration of source transistor 310, capacitor 326, and sink transistor 330 with respect to electrodes 304 and 306. Voltage supply 302 represents a voltage sensed between two electrodes, electrode 304 and electrode 306 of IMD 4. Overvoltage protection circuitry 308 is situated between electrodes 304 and 306 and current source transistor 310 and current sink transistor 330. In some examples, voltage supply 302 may be high enough to trigger overvoltage protection circuitry 308. In examples where voltage supply 302 is not high enough to trigger overvoltage protection circuitry 308, the current from voltage supply 302 charges capacitor 326, which in turn raises the voltage at overvoltage protection circuitry 308 until the voltage threshold of the overvoltage protection circuitry is exceeded. In some examples capacitor 326 may have a capacitance of between approximately 0.5 uF to 10 uF. In some examples, capacitor 326 may have a capacitance of approximately 1 uF. In some examples, the characteristics of capacitor 326 are selected based on the trigger voltage of overvoltage protection element 308. For example, the capacitance of capacitor 326 may be selected in order to insure that the capacitor is rated at least 1.5 times the trigger voltage of the overvoltage protection element 308.

In some examples, current source transistor 310 is a PMOS transistor. Source transistor 310 may be a current source cascode. The gate 312 of source transistor 310 may be set to a source cascode bias during stimulation. When circuit 300 is in a stimulation mode switch 322 is closed and node 314 is source of the transistor 310. Node 314 received current from current mirror array 324. Current mirror array 324 provides current to the source node 314 of transistor 310. Current mirror array 324 may be connected to battery 328. Source cascode bias turns on the transistor allowing creating a channel from source node 314 to drain node 318. During a stimulation mode, node 318 of transistor is a drain. During the stimulation mode, the switch 320 is open. Further, during the stimulation mode, the body node 316 is connected to the source 314 through a switch (not shown).

When circuit 300 is in a non-stimulation mode, as shown in FIG. 3, switch 320 is closed and switch 322 is open. In this configuration, gate 312 is driving to the voltage at node 316 by a PMOS switch (not shown). The gate on the PMOS switch is grounded turning that FET on and shorting gate node 312 to node 344. In the presence of voltage 302, the voltage at node 318 rises. When the voltage at node 318 is approximately a diode above the voltage at 316 an internal diode is activated and current flow from node 318 to node 316. Node 316 of transistor 312 may be connected to internal node 344 when switch 320 is closed. The configuration of transistor 310 in the presence of a high voltage at node 318 is illustrated in greater detail in FIG. 5A below.

When voltage 302 is present, current flows from electrode 304 to capacitor 326. Internal node 344 is configured to allow the voltage at capacitor 326 to rise above the voltage supply 302. This current charges capacitor 326, which in turn raises the current at the ground node 342. Ground node 342 is connected to substrate node 338 of sink transistor 330. When voltage 302 is present gate 332 of sink transistor 332 is shorted to ground when stimulation is not being applied with an additional NMOS switch (not shown). The gate of the NMOS switch is tied high turning that FET on and shorting the gate to ground. The presence of voltage 302 pulls the voltage at node 334 below ground. When the voltage decreases to approximately a diode below ground a diode between node 338 and node 334 of transistor 330 is activated, allowing current to flow from capacitor 326 to overvoltage protection array 308. The additional current drives the voltage at node 334 even farther below ground, thereby increasing the voltage drop between electrodes 304 and 306 until the voltage threshold of overvoltage protection circuitry 308 is met.

Sink transistor 330 may be a sink cascode. The node 336 is connected to a sink mirror array 340. During the stimulation mode, node 336 is a source node and node 334 is a sink node. During the stimulation mode gate 332 of transistor 332 is set to sink cascode bias, which allows for normal operation of transistor 330.

During the non-stimulation mode, the current path through nodes 318 and 316 of transistor 310 and nodes 338 and 334 of transistor 330, allow the continuous flow of current from supply 302 at a level which is able to maintain overvoltage protection circuitry 308 in an on configuration. In some examples, overvoltage protection circuitry may include both trigger circuitry and an overvoltage protection element. In other examples, overvoltage protection circuitry 308 may include an overvoltage protection element that does not need additional trigger circuitry. Overvoltage protection circuitry 308 may be a silicon-controlled rectifier (SCR)-type device. Overvoltage protection circuitry 308 may clamp the voltage that reaches the rest of the circuit when it is in the on configuration. In some examples, the overvoltage protection circuitry 308 clamps the voltage at approximately 3 volts. As briefly discussed above, overvoltage protection array 308 may have a voltage trigger. When the voltage difference between the nodes on each side of overvoltage protection array 308 exceeds a predetermined threshold, a protection element breaks over and begins to clamp the voltage. The clamp may be maintained as long as a sufficient current is maintained at a predetermined level. In some examples, the voltage threshold is between approximately 17 volts and approximately 24 volts.

Figure 4:
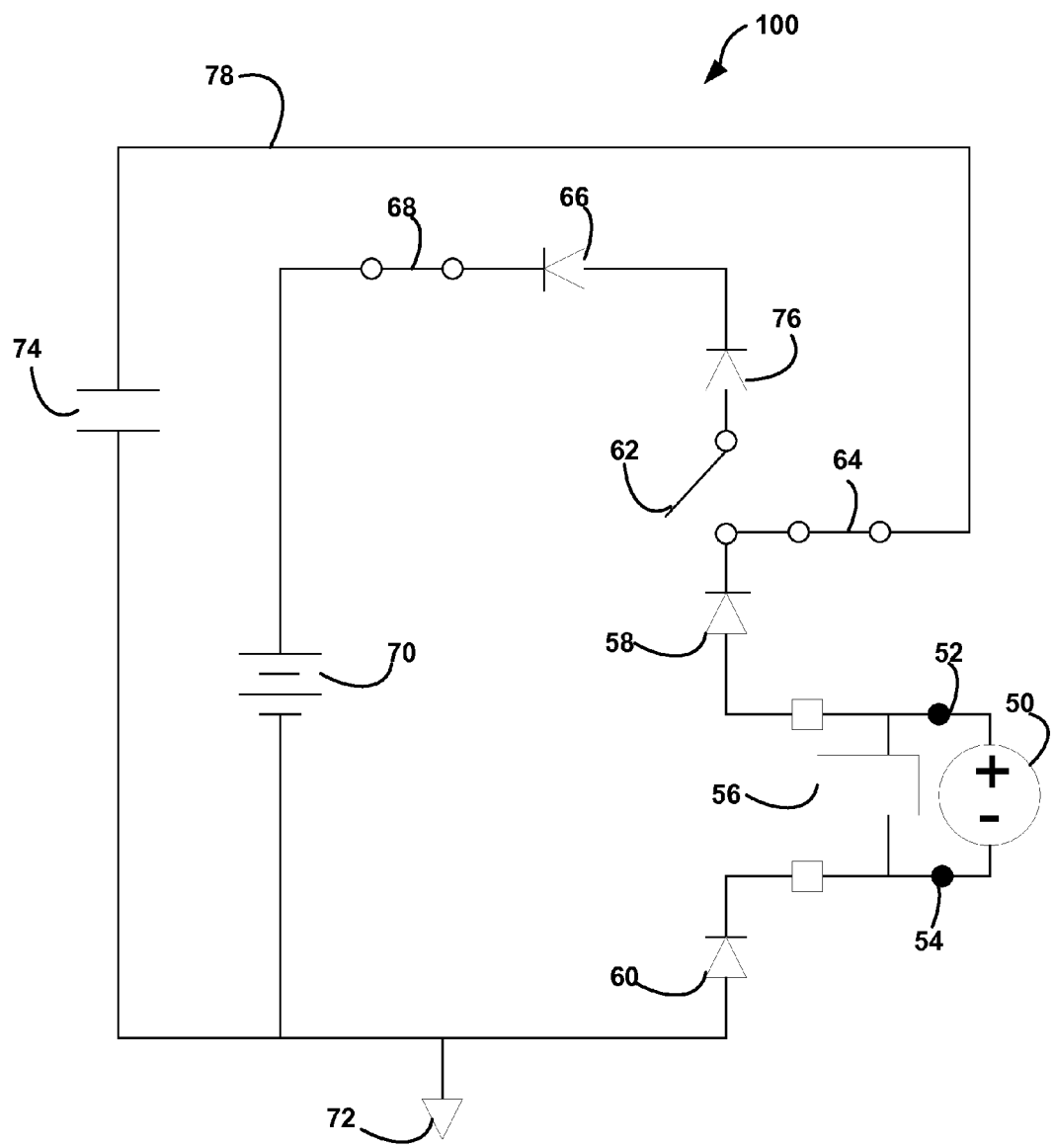
FIG. 4 is a schematic diagram of an example circuit within an implantable stimulator, including overvoltage protection circuitry, consistent with this disclosure.

FIG. 4 is a schematic diagram of an example circuit 100 within implantable stimulator 4, including overvoltage protection circuitry, consistent with this disclosure. Example circuit 100 is simplified to primarily show the current path used when voltage supply 50 is present. Voltage supply 50 represents a voltage sensed between two electrodes, electrode 52 and electrode 54 of IMD 4. Overvoltage protection circuitry 56 is situated between electrodes 52 and 54 and current source diode 58 and current sink diode 60. In some examples, current source diode 58 bypasses a current source cascode in the presence of a voltage supply 50 and current sink diode 60 bypasses a current sink cascode. In other examples, current source diode 58 and current sink diode 60 are diodes between a body and a source of a transistor. In other words, current source diode 58 and current sink diode 60 may be found within transistors such as transistors 310 and 330 of FIG. 3, and only present when voltage supply 50 is present. In such examples, during normal operation current source diode 58 is off, and a transistor such as the PMOS transistor 310 shown in FIG. 3 is operating as a transistor, and current sink diode 60 is off and a transistor such as NMOS transistor 330 also shown in FIG. 3.

The schematic as shown in FIG. 4 depicts the current paths by which overvoltage protection circuitry 56 may be triggered even when voltage 50 is below the voltage threshold of overvoltage protection circuitry 56. In some examples, current source diode 58 is within a current source cascode and current sink diode 60 is within a current sink cascode. Current sink diode 60 is located between electrode 54 and ground 72. When diode 58 is activated internal node 78 is configured to allow the voltage at internal node 78 to rise above voltage 50, thereby allowing the voltage drop over capacitor 74 to exceed the voltage trigger of Overvoltage protection circuitry 56. This allows overvoltage protection circuitry 56 to be triggered even when voltage 50 is below the voltage trigger threshold of the overvoltage protection circuitry 56.

Overvoltage protection circuitry 56 may include a silicon-controlled rectifier (SCR)-type device. Overvoltage protection circuitry 56 may clamp the voltage that reaches the rest of the circuit. In some examples, the overvoltage protection circuitry 56 clamps the voltage at approximately 3 volts. When the voltage is clamped, the current from voltage 50 is dissipated before it can reach the internal integrated circuit (not shown). The overvoltage protection circuitry 56 may have a voltage threshold trigger. When the voltage threshold is reached, the protection element breaks over and begins to clamp. The clamp may be maintained as long as a sufficient current is maintained at a predetermined level. The current is maintained at the predetermined level by voltage 50 (external stimulus). Current source 58 is situated within circuit 100 in a manner that allows current from voltage 50 to charge capacitor 74. In some examples, a configuration of circuit 100 wherein switch 64 is closed and switch 62 is open is non-stimulation mode. In some examples switches 62 and 64 in combination are a well switcher. This configuration does not allow for the delivery of stimulation by electrode 52, 54, but does allow overvoltage protection circuitry 56 to fire in the presence of a high voltage electrical pulse. The configuration shown in FIG. 4 allows current to flow from electrode 52, to capacitor 74, and back towards electrode 54.

In some configurations, not shown, switch 62 is closed and switch 64 is open. This allows current provided by battery 70 to flow to electrode 52. However, if an electrical pulse was applied across electrodes 52 and 54 while switch 64 was open, the current would not be able to charge capacitor 74, and therefore overvoltage protection circuitry 56 may not fire. In this configuration additional current sources 66 and 76 also help control and provide current for stimulation pulses. In the configuration shown, with switch 68 closed, a capacitor (not shown) associated with current source 66 is being charged.

Figure 5A:
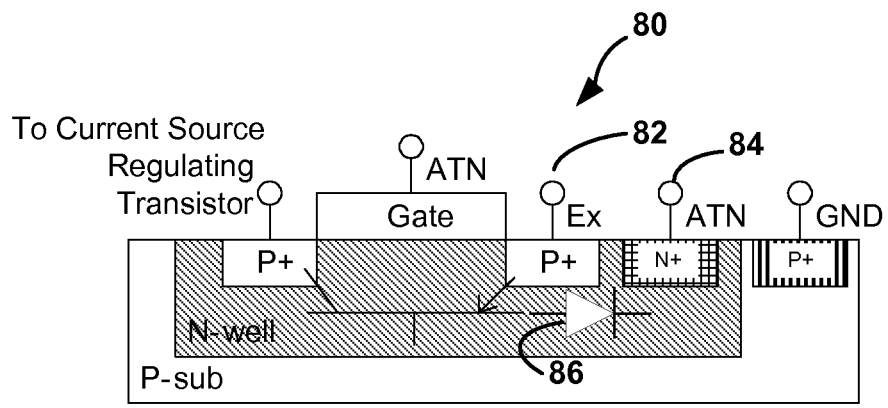
FIG. 5A is a diagram illustrating a current source (PMOS) transistor with a parasitic bipolar transistor that forms a current path for overvoltage protection circuitry consistent with this disclosure.

FIG. 5A is a diagram illustrating a current source (PMOS) transistor 80 with the parasitic bipolar (PNP) transistor that forms a current path for overvoltage protection circuitry consistent with this disclosure. The transistor 80 as depicted in FIG. 5A allows for charging of the capacitor 74 of FIG. 4 in the presence of a large electrical pulse. In the presence of an electrical pulse which is providing parasitic charging of capacitor 74, capacitor 74 provides current flow above a level need to maintain the protection element in an on-state where the protection element is clamping the voltage at a predetermined level. In the presence of an electrical pulse, a high voltage is present at source node 82 coming from electrode 52. The result is that when the voltage at node 82 is higher than the voltage at node 84, which is connected to capacitor 74, the PN junction (or diode) 86 within the PMOS transistor 80 is turned on. When diode 86 is turned on current flows out of node 84 to capacitor 74. The set-up allows for additional current flow to capacitor 74, without dragging down or limiting the voltage out of node 84. In some examples, transistor 80 is current source transistor 310 of FIG. 3, and diode 86 is between nodes 318 and 316 of FIG. 3. In some examples, diode 86 is the diode used to depict current source 58 in the simplified schematic of FIG. 4. During normal functioning of circuit 100, including during the application of stimulation, for example, node 82 is a drain. The presence of the large current or voltage at node 82 causes the PMOS transistor to function in a way not normally intended. In particular, in normal circuit design it is desirable to insure that the diode 86 is not turned on. However, the circuit 100 is set up to exploit what would normally be considered undesirable behavior.

Figure 5B:
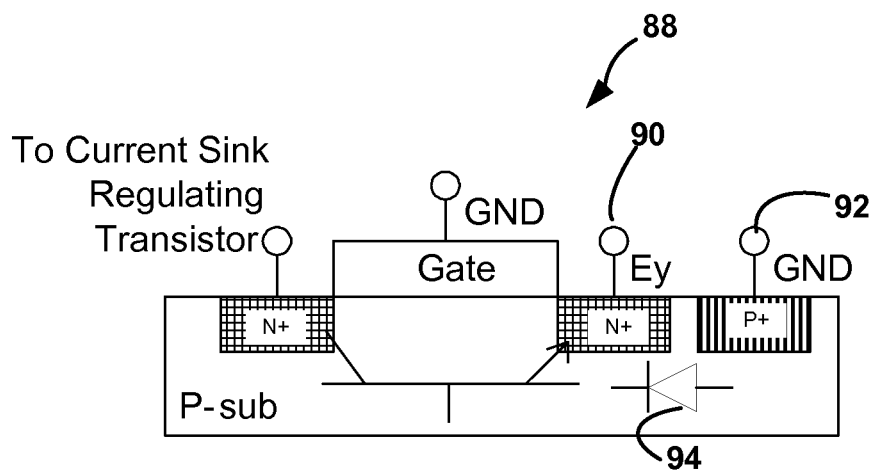
FIG. 5B is a diagram illustrating a current sink (NMOS) transistor with a parasitic bipolar transistor that forms a current path for overvoltage protection circuitry is exploited by a circuit consistent with this disclosure.

FIG. 5B is a diagram illustrating a current sink (NMOS) transistor 88 with a parasitic bipolar transistor forms a current path for overvoltage protection circuitry is exploited by a circuit consistent with this disclosure. The transistor 88 allows for charging of capacitor 74 and triggering of a protection element, such as overvoltage protection circuitry 56 of FIG. 4. In examples where a large voltage or current is sensed at electrodes 52 and 54. When the voltage at node 82 of FIG. 5A gets above a predetermined level, the voltage at node 90 may be forced below ground 92. In some examples the voltage at node 90 goes below approximately a diode below ground. In some examples the voltage at node 90 may go between 500 and 700 mV below ground. When this occurs the PN junction (or diode) 94 is turned on, and current flows out of node 90 towards protection element 56. This allows the charged capacitor 74 to force a higher voltage between electrode 52 and 54 in order to cause the overvoltage protection element 56 to turn on, and maintain the overvoltage protection element in the on configuration while current continues to flow above a predetermined level from the voltage source 50. In some examples, transistor 88 is current sink transistor 330 of FIG. 3, and diode 94 is between nodes 338 and 334 of FIG. 3. In some examples, diode 94 is the diode used to depict current sink 60 in the simplified schematic of FIG. 4. The presence of a large voltage difference between nodes 82 and 90 causes NMOS transistor 88 to function in a way not normally intended. In particular, in normal circuit design it is desirable to insure that the diode 94 is not turned on. However, the circuit 100 is set up to exploit what would normally be considered undesirable behavior.

Figure 6:
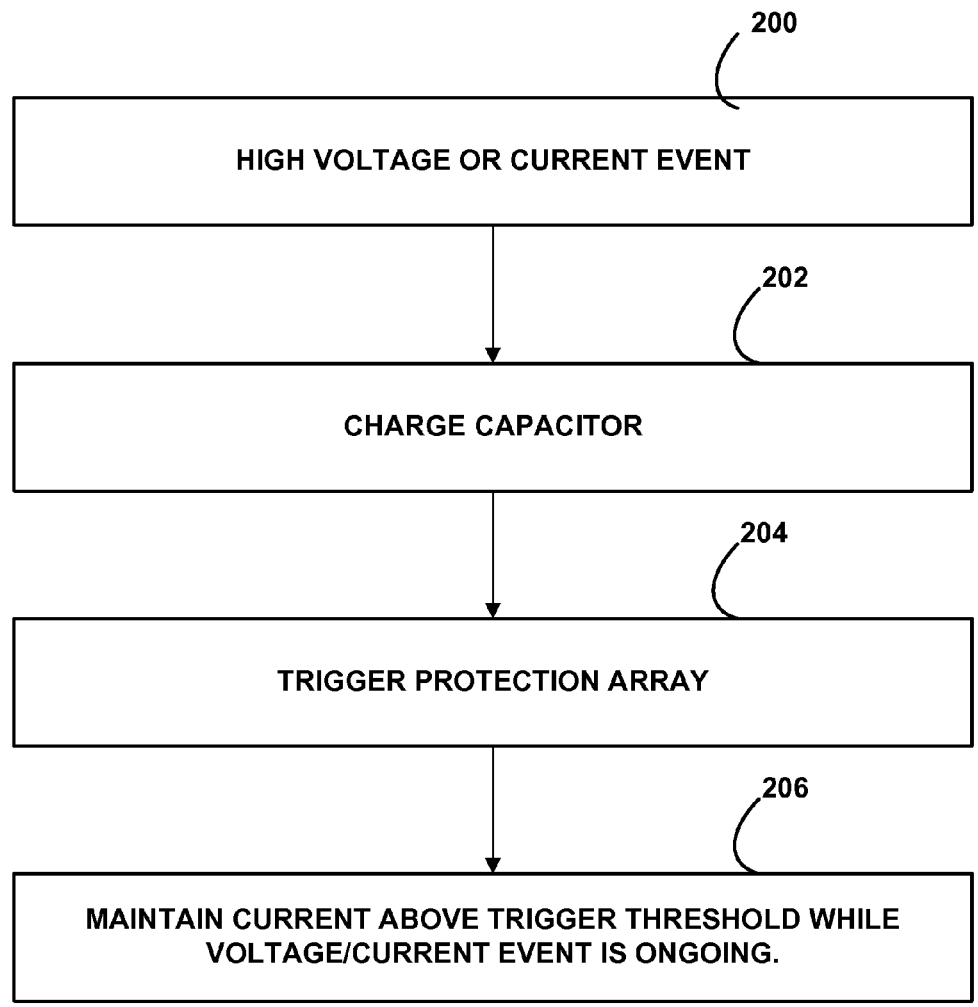
FIG. 6 is a flow chart illustrating triggering of overvoltage protection element consistent with this disclosure.

FIG. 6 is a flow chart illustrating an example triggering of the overvoltage protection element consistent with this disclosure. A high voltage or current event (200) results in a large voltage or current across two electrodes 52 and 54 of IMD 4. The current or voltage from the high voltage or current event charges a capacitor (202) within the circuitry of IMD 4. In some examples, the capacitor charged is capacitor 74. Capacitor 74 may be charged by a current path created with one or more of the circuit elements in the presence of the high voltage or current event. For example, capacitor 74 may be charged by a path include parasitic capacitance from at least one of a current source or a current sink within the circuit 100. For example, parasitic capacitance from current source 58 and current sink 60 may create the current path which charges capacitor 74. Once capacitor 74 is charged above a predetermined level, the voltage as the protection array is enough to trigger the protection array (204). For example, the protection array may be triggered when the voltage at the trigger node is between 17 and 24 V. In some examples, the trigger voltage may be approximately 19 V. This voltage may be achieved by charging capacitor 74. When protection array 56 is triggered, protection array 56 clamps the voltage of the circuit at 3V. The circuit maintains the current above a second trigger threshold while the voltage or current event is ongoing (206). In some examples, circuit 100 maintains the current at a level above the maintenance threshold through the continuous charging and discharging of capacitor 74 while the voltage or current event is ongoing. In other words, once the protection array is turned on or "breaks over" the protection array stays on as long at the current is maintained above a predetermined level by the voltage source 50. In some examples the predetermined current level, or hold current, is approximately 1 mA to 10 mA.

Figure 7:
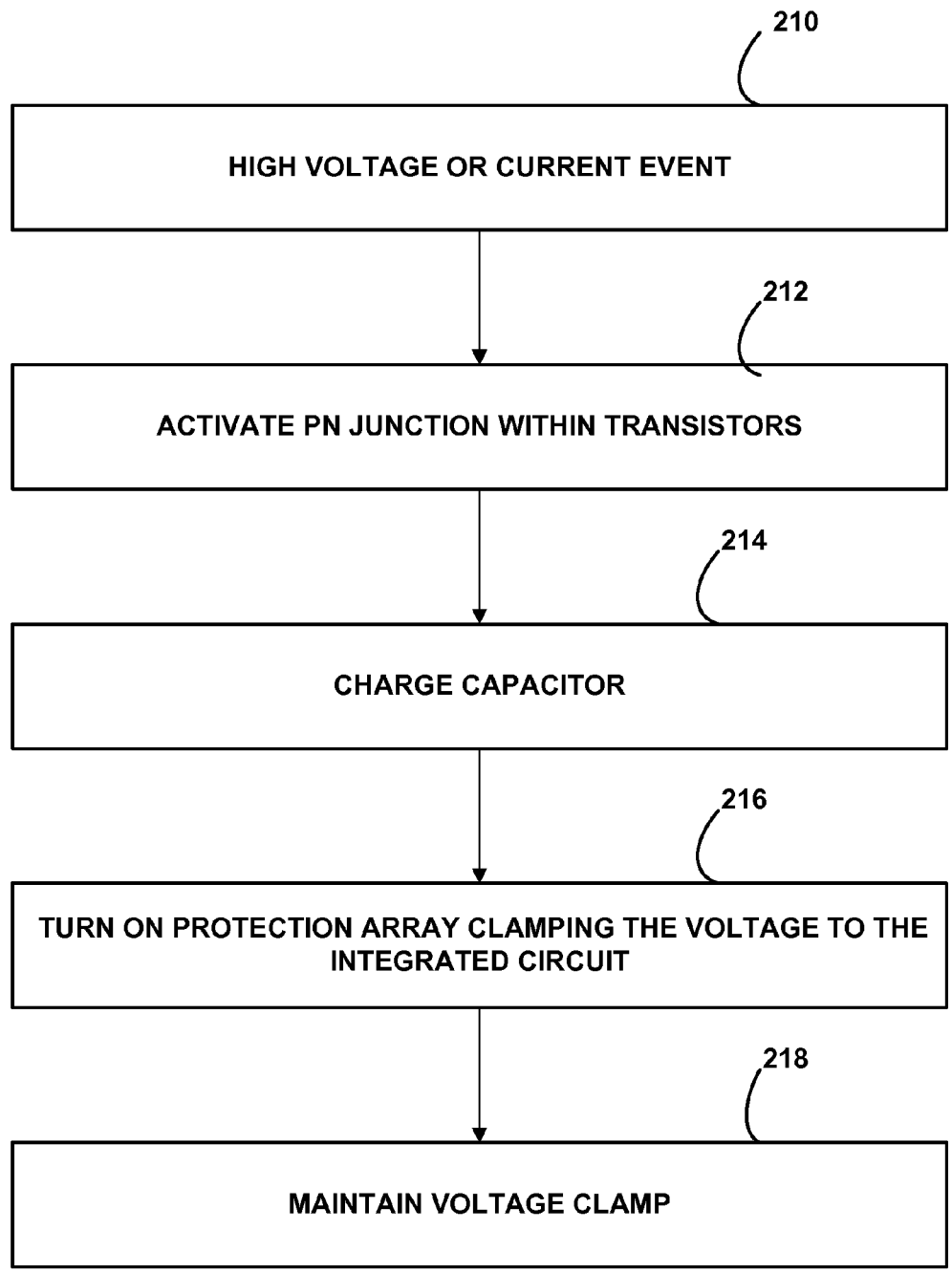
FIG. 7 is a flow chart illustrating an example triggering of an overvoltage protection element consistent with this disclosure.

FIG. 7 is a flow chart illustrating an example triggering of an overvoltage protection element consistent with this disclosure. A high voltage or current event (210) results in a large voltage or current across two electrodes 52 and 54 of IMD 4. The high voltage event may be the result of electrocautery or a defibrillation pulse, for example. The high voltage event at the electrodes modifies the functioning of one or more transistors within circuit 100 by activating a PN junction within one or more transistors (212). The PN junction that is activated is a junction that is not normally activated during the regular functioning of the transistor. For example, the PN junction may be one between a drain and a body, which if activated while the transistor was performing ifs function during application of stimulation to patient 6, would result in a malfunction. However, circuit 100 is designed to exploit the activation of a first PN junction to allow current to flow to capacitor 74. This may occur when the voltage of the node connected to an electrode sensing the voltage event rises above the voltage of the node which is connected to capacitor 74. In some examples, a second PN junction in a second transistor is also activated. The second PN junction is activated when the voltage at a node connected to the transistor and to a second electrode sensing the high voltage event is driven below ground. The activation of the second PN junction allows for the flow of current from capacitor 74 to protection array 56.

The flow of current through the first activated PN junction to capacitor 74 charges capacitor 74 (214). In some examples, capacitor 74 is charged to a level enabling the application of between approximately 17-24 volts to overvoltage protection element 56. Once charged, capacitor 74 increases the voltage between electrodes 52 and 54 thereby causing overvoltage protection element 56 to turn on. In some examples, the voltage between electrodes 52 and 54 is raised approximately two diodes above the voltage of capacitor 74. Overvoltage protection circuitry 56 has a threshold between approximately 17-24 Volts. When the voltage at the protection array reaches the threshold or breakdown voltage, the voltage turns on overvoltage protection circuitry 56 thereby clamping the voltage to the integrated circuit (216). In some examples, the voltage is clamped between approximately 3 to 4 volts. In some examples, the overvoltage protection circuitry 56 shunts current in order maintain the clamped voltage. As long as the current between electrodes 52 and 54 is above a predetermined level, overvoltage protection element 56 will maintain the voltage clamp (218). The current level will be above the predetermined level for approximately the duration of the high voltage event. The predetermined level of current may be between approximately 1 mA and 10 mA.

Various examples of the disclosure have been described. These and other examples are within the scope of the following claims.

The invention claimed is:

1. A medical device comprising:
   a first implantable electrode;
   a second implantable electrode;
   a current source transistor configured to source electrical stimulation via the first implantable electrode;
   a current sink transistor configured to sink the electrical stimulation via the second implantable electrode;
   a capacitor configured to receive, via a parasitic PN junction of the current source transistor, current generated by a first voltage across the first implantable electrode and the second implantable electrode, the first voltage from an external source, and store a second voltage with the received current; and
   an overvoltage protection element configured to shunt current between the first implantable electrode and second implantable electrode if the second voltage stored by the capacitor exceeds a threshold voltage of the overvoltage protection element.

2. The device of claim 1,
   wherein each of the current source transistor and the current sink transistor creates a respective current path to the capacitor to receive the current generated by the first voltage across the first implantable electrode and the second implantable electrode.

3. The device of claim 1, wherein the current source transistor is configured as a current source cascode.

4. The device of claim 1, wherein the current sink transistor is configured as a current sink cascode.

5. The device of claim 1, wherein the overvoltage protection element is a silicon-controlled rectifier.

6. The device of claim 1, wherein the threshold voltage is a voltage value selected from a range between 17 to 24 volts.

7. The device of claim 5, wherein the overvoltage protection element is further configured to continue shunting current as long as a current from the external source to the overvoltage protection element is above a predetermined level.

8. The device of claim 1, wherein the overvoltage protection element is configured as a voltage clamp to maintain a voltage between the first implantable electrode and the second implantable electrode between 3 to 4 volts.

9. The device of claim 1, further comprising a stimulation generator configured to generate electrical stimulation via at least one of the first and second implantable electrodes.

10. A method comprising:
    detecting a first voltage between a first implantable electrode and a second implantable electrode, the first voltage generating a current, the first voltage from an external source;
    creating a current path between
      the first implantable electrode,
      a current source transistor configured to source electrical stimulation via the first implantable electrode;
      a capacitor;
      a current sink transistor configured to sink the electrical stimulation via the second implantable electrode; and the second implantable electrode,
wherein a parasitic PN junction of the current source transistor creates a respective portion of the current path to the capacitor;
storing at the capacitor, a second voltage from the current received at the capacitor via the current path; and
activating an overvoltage protection element configured to shunt current between the first implantable electrode or second implantable electrode if the second voltage stored by the capacitor exceeds a threshold of the overvoltage protection element.

11. The method of claim 10, wherein the current source transistor is a current cascode.

12. The method of claim 10, wherein the current sink transistor is a sink cascode.

13. The method of claim 10, wherein the overvoltage protection element is a silicon-controlled rectifier.

14. The method of claim 10, wherein the threshold voltage is a voltage value selected from a range between 17-24 volts.

15. The method of claim 13, further comprising:
shunting current between the first and second implantable electrodes while a magnitude of the shunted current is above a predetermined threshold.

16. The method of claim 10, wherein the overvoltage protection element is configured as a voltage clamp to maintain a voltage between the first implantable electrode and the second implantable electrode between 3 to 4 volts.

17. The method of claim 10, further comprising delivering electrical stimulation via at least one of the first and second implantable electrodes.

18. A circuit comprising:
a first implantable electrode;
a second implantable electrode;
a first parasitic PN junction diode of a first transistor configured to allow current, generated by a first voltage across the first implantable electrode and the second implantable electrode, to flow from the first implantable electrode to an internal node of the circuit, wherein the internal node is configured to allow a second voltage of the internal node to raise in response to the current generated by the first voltage;
a capacitor attached to the internal node and configured to receive, via the internal node, a second current at the internal node and store a third voltage with the received second current; and
an overvoltage protection element configured to shunt current between the first implantable electrode or second implantable electrode if the third voltage store by the capacitor exceeds a threshold voltage of the overvoltage protection element.

19. The circuit of claim 18, further comprising:
a second parasitic PN junction diode of a second transistor between the capacitor and the second implantable electrode, the diode configured to allow a third current to flow from the capacitor to the overvoltage protection element.

20. The circuit of claim 19, wherein the overvoltage protection element is configured as a voltage clamp to maintain a voltage between the first implantable electrode and the second implantable electrode between 3 to 4 volts.

21. A medical device comprising:
means for detecting a first voltage between a first implantable electrode and a second implantable electrode, the first voltage generating a current, the first voltage from an external source;
means for creating a current path between
the first implantable electrode,
a current source transistor configured to source electrical stimulation via the first implantable electrode;
a capacitor;
a current sink transistor configured to sink the electrical stimulation via the second implantable electrode; and
the second implantable electrode,
wherein at least a parasitic PN junction of the current source transistor creates a respective portion of the current path to the capacitor;
means for storing, at the capacitor, a second voltage from the current received at the capacitor via the current path; and
means for activating an overvoltage protection element configured to shunt current between the first implantable electrode or second implantable electrode if the second voltage stored by the capacitor exceeds a threshold of the overvoltage protection element.

* * * * *